United States Patent [19]
Tewari et al.

[11] Patent Number: 6,004,267
[45] Date of Patent: Dec. 21, 1999

[54] METHOD FOR DIAGNOSING AND STAGING PROSTATE CANCER

[75] Inventors: Ashutosh Tewari; Perinchery Narayan, both of Gainesville, Fla.

[73] Assignee: University of Florida, Gainesville, Fla.

[21] Appl. No.: 09/036,307

[22] Filed: Mar. 6, 1998

Related U.S. Application Data

[60] Provisional application No. 60/039,917, Mar. 7, 1997.
[51] Int. Cl.$^6$ .......................................................... A01B 5/00
[52] U.S. Cl. ............................................ 600/300; 128/925
[58] Field of Search ............................... 600/377; 395/22; 364/401, 413.2

[56] References Cited

U.S. PATENT DOCUMENTS

| 5,214,746 | 5/1993 | Fogel et al. . |
|---|---|---|
| 5,590,665 | 1/1997 | Kanai . |

FOREIGN PATENT DOCUMENTS

| 9612187 | 4/1996 | WIPO . |
|---|---|---|
| 9712247 | 4/1997 | WIPO . |

OTHER PUBLICATIONS

Kattan, M. W. et al. (1997) "Applying A Neural Network To Prostate Cancer Survival Data" Intelligent Data Analysis In Medicine and Pharmacology, pp. 295–306.

Prater, J. S. et al. (1992) "Segmenting Ultrasound Images of the Prostate Using Neural Networks" Ultrasonic Imaging 14;159–185.

Oesterling, J. E., (1995) "Using Prostate–Specific Anitgen to Eliminate Unnecessary DiagnosticTests: Significant Worldwide Economic Implications" Urology 46:26–33.

Oesterling, J. E., (1993) "Using PSA to Eliminate the Staging Radionuclide Bone Scan " Urol. Clin. North Am. 20:705–711.

Partin, A. W. et al. (1993) "The Use of Prostate Specific Antigen, Clinical Stage and Gleason Score to predict Pathological Stage in Men with Localized Prostate Cancer" J. Urol. 150:110–114.

Partin, A. W. et al. (1994) "Re: The Use of Prostate Specific Antigen, Clinical Stage and Gleason Score to Predict Pathological Stage in Men with Localized Prostate Cancer" J. Urol. 152:172–173.

Narayan, P. et al. (1995) "The Role of Transrectal Ultrasound–Guided Biopsy–BAseddd Staging,PreoperativeSerum Prostate–Specific Antigen, and Biopsy Gleason Score in Prediction of Final Pathologic Diagnosis in Prostate Cancer" Urology 46:205–212.

Badalament, R. et al. (1996) "An Algorithm for Predicting Nonorgan Confined Prostate Cancer Using the Results Obtained from Sextant Core Biopsies with Prostate Specific Antigen Level" J. Urol. 156:1375–1380.

(List continued on next page.)

*Primary Examiner*—Cary O'Connor
*Assistant Examiner*—Pamela L. Wingood
*Attorney, Agent, or Firm*—Saliwanchik, Llyod & Saliwanchik

[57] ABSTRACT

The subject invention provides a method for diagnosing prostate cancer and determining preoperatively the pathological stage in patients with prostate cancer. The methods described herein can be used for prediction of margin positivity, seminal vesicle (S.V.) involvement, and lymph nodal (L.N.) involvement in patients with clinically localized prostate cancer. The method includes use of a neural network which provides prostate cancer stage information for a patient based upon input data which includes the patient's preoperative serum PSA, biopsy Gleason score, and systemic biopsy-based information. Its positive predictive value (PPV), negative predictive value (NPV), and accuracy are superior to that of current nomograms in use. Use of this method can result in enormous cost savings by accurately diagnosing patients with prostate cancer and by avoiding multiple imaging tests and expensive surgery in unindicated patients.

26 Claims, 5 Drawing Sheets

OTHER PUBLICATIONS

Wasserman, P. (1993) Advanced Methods in Neural Computing: Theory and Practice, Van Nostrand, New York, pp. 1–60.

Ravery, V. et al. (1994) "Predictive Value of Pathological Features for Progression after Radical Prostatectomy" Eur. Urol. 26:197–201.

Snow, P. B. et al. (1994) *Artificial Neural Networks in the Diagnosis and Prognosis of Prostate Cancer:* A Pilot Study J. Urol. 1923–1926.

Webber, W. R. et al. (1996) An approach to seizure detection using an artificial neural network (ANN) Electroencephalogr. Clin. Neurophysiol. 98:250–272.

METHOD FOR DIAGNOSING AND STAGING PROSTATE CANCER

This application claims benefit of provisional application No. 60/039,917 filed Mar. 07, 1997.

FIELD OF THE INVENTION

The present invention is generally related to diagnosing and staging of prostate cancer using genetic adaptive neural networks.

BACKGROUND OF THE INVENTION

Prostate cancer is one of the most common cancers in men, comprising approximately 33% of all cancers. In 1996, 317,000 new patients will be diagnosed with prostate cancer. Fifty percent of these (158,550) will undergo radical prostatectomy. Statistics indicate that 1.5 billion dollars are spent as direct medical expenses and an additional 2.5 billion dollars as indirect costs in the management of prostate cancer. It is also anticipated to further increase due to the steep rise in population of patients older than 65 years. Current estimates are that 85,800 radical prostatectomies are performed annually.

At present, radical prostatectomy is clearly the most effective treatment for prostate cancer resulting in a disease-free survival (DFS) at 10 years in up to 85% of patients. However, cure is only possible if the cancer is organ confined. Several long-term studies of radical prostatectomy show that biochemical failure at 10 years is seen in as many as 58% of patients with positive margins, 57% with seminal vesicle-positivedisease, and 100% with lymph nodal disease. It is therefore essential to accurately stage prostate cancer and avoid radical interventions to potentially incurable patients. Inaccurate staging adds significantly to the cost of managing prostate cancer. It is therefore imperative to construct accurate and cost-effective staging tools. Currently, however, understaging of prostate cancer occurs in 40–60% of clinically localized prostate cancer. Margin-positive disease remains the biggest problem confronting clinicians attempting surgical management of prostate cancer. In recent studies, the incidence of margin positive disease after radical prostatectomy is very high (37– 63%; mean 45%). The mean incidence of margin positivity and seminal vesicle involvement is 17–47%, while nodal involvement is 2–10.5%. Although an overwhelming number of staging studies are currently available to the clinician, including digital rectal examination (DRE), prostate specific antigen (PSA), prostate specific antigen density (PSAD), PSAD corrected for transition zone of prostate (PSAT), sextant prostate biopsy, transrectal ultrasound guided (TRUS) capsular and seminal vesicle biopsies, molecular staging (PCR-PSA), endorectal MRI, pelvic CT, CT-guided lymph node biopsies, antigen directed monoclonal antibodies (Onco Seint; "CYTOGEN"), bone scintigraphy and staging lymph node dissection, none are very accurate. This lack of sensitivity and specificity results in many patients undergoing multiple staging procedures. These multiple staging procedures and resultant unindicated surgical interventions currently add significantly to the cost of managing prostate cancer.

Because of the dire need for strategies to reduce staging costs, several investigators have studied this issue. One of the earliest studies was by Oesterling and associates, who reported on the role of serum PSA in reducing the need for bone scintigraphy (Oesterling, J. E. [1995] *Urology* 46:26–33; Oesterling, J. E. [1993] *Urol. Clin. North Am.* 20:705–711). A number of other studies indicating the lack of need of certain single modalities of staging such as bone scintigraphy and node dissection prompted several investigators to study a combination of variables to construct relatively uncomplicated nomograms for clinicians managing prostate cancer. Several nomograms have been proposed to predict probabilities of extracapsular and metastatic disease. These nomograms however are variable and not highly accurate. Examples of such nomograms include those by Partin, Badalament, and Narayan (Partin, A. W., J. Yoo, H. B. Carter et al. [1993] *J. Urol.* 150:110–114; Partin, A. W., P. C. Walsh [1994] *J. Urol.* 152:172–173;Narayan, P., V. Gajendran, S. P. Taylor et al. [1995] *Urology* 46:205–21; R., M. Miller, P. Peller et al. [1996] *J. Urol.* 156:1375–1380). While Partin and associates utilize the large database of accurately studied prostate cancer patients at Johns Hopkins Institute, its major drawback is the use of DRE to differentiate T2a/b and T2c patients. A second problem may be the small-sized cancers and select population seen at Johns Hopkins Institute. Recently, Badalament and associates have constructed a backwards stepwise logistic regression algorithm based on nuclear imaging, DNA ploidy, nuclear grade, serum PSA, percent of tumor involvement, number of positive sextant cores, preoperative Gleason score, and more than 5% of base and/or apex involvement in 210 patients (Badalament et al., supra). They report an 86% sensitivity, 71% specificity, 73% positive predictive value, and 85% negative predictive value. Their input data required several specialized investigations such that its day to day utility and cost-effectiveness remain to be established. Some of the input variables they used such as DNA ploidy are also very controversial in that several investigators have questioned their utility. They also have a relatively small number of patients (N=200), so the utility needs testing in large numbers. In the other study (N=813), pooled patient data from two major universities was combined with data from a major HMO as well as data from the private practice of prominent urologists. (R) This series, however, used TRUS-guided systemic biopsy data rather than DRE to clinically stage patients.

Neural networks utilize the concept of artificial intelligence (Niederberger, C. S., L. I. Lipshultz, D. J. Lamb [1993] *Fertil. Steril.* 60:324–330; Niederberger, C. S. [1995] *J. Urol.* 153; Wasserman, P. [1993] *Neural Computing: Theory and Practice,* Van Nostrand Reinhold, New York, pp. 1.1–11; Wasserman, P. [1993] *Advanced Methods in Neural Computing,* Van Nostrand Reinhold, New York, pp. 1–60; Fu, L. [1994] *Neural Networks in Computer Intelligence,* McGraw-Hill, Inc., New York, pp. 155–166). Attempts have been made to apply this technology to certain medical problems, including the prediction of myocardial infarction in patients using family history, body weight, lipid profile, smoking status, blood pressure, etc. (Lamb, D. J., C. S. Niederberger [1993] *World J. Urol* 11: 129–136; Patterson, P. E., [1996] *Biomed Sci. Instrum.* 32:275–277; Pesonen, E. M. Eskelinen, M. Juhola [1996] *Int. J. Biomed Comput.* 40:227–233; Ravery, V., L. A. Boccon Gibod, A. Meulemans et al. [1994] *Eur. Urol.* 26:197–201; Snow, P. B., D. S. Smith, W. J. Catalona [1994] *J. Urol.* 1923–1926;Stotzka, R., R. Manner, P. H. Bartels, D. Thompson [1995] *Anal. Quant. Cytol Histol.* 17:204–218; Yoshida, K., T. Izuno, E. Takahashi et al. [1995] *Medinfo* 1:838–842; Webber, W. R., R. P. Lesser, R. T. Richardson et al. [1996] *Electoencephalogr. Clin. Neurophysiol.* 98:250–272). Snow and associates also attempted to use a neural network in the detection of prostate cancer and prediction of biochemical failure following radical prostatectomy (Snow et al., supra).

Several investigators have attempted to construct probability tables and nomograms by combining the results of the above-mentioned tests (Partin et al., supra; Partin and Walsh, supra; Narayan et al., supra). As previously discussed, these nomograms only provide a probability percentage, but currently there are no recommendations about cut points for these percentages which can help patients and physicians in decision making. Our testing of these nomograms using a 15 to 20% acceptable risk for margin positive disease revealed a positive predictive value (PPV), negative predictive value (NPV), sensitivity, specificity, and accuracy of 38%, 70%, 72%, 36%, and 48%, respectively for predicting margin positivity in prostate cancer. A cutoff point of 5% probability for the nomogram predicting S.V. positivity resulted in a PPV, NPV, sensitivity, specificity, and accuracy of 9%, 97%, 73%, 55%, and 56%, respectively. A cut off point of 5% probability for the nomogram predicting L.N. positivity resulted in statistical measures of 9%, 75%, 66%, and 67%, respectively.

The currently available staging modalities for prostate cancer are rather inadequate for accurate staging. Only 60% of cancers clinically diagnosed to be locally confined turn out to be so on final pathology. Accurate preoperative staging is important; patients with positive margins with or without seminal vesicle involvement and lymph nodal spread have a distinctly poorer prognosis than those with organ confined disease. Radical prostatectomy in patients with organ confined disease on final pathological analysis results in survival comparable to that of age-matched controls without prostate cancer. Therefore, it is easier to make a distinction between patients with organ confined versus margin positive and regional disease for management decisions.

BRIEF SUMMARY OF THE INVENTION

The subject invention provides a method for diagnosing prostate cancer and determining preoperatively the pathological stage in patients with prostate cancer. The methods described herein can be used for prediction of margin positivity, seminal vesicle (S.V.) involvement, and lymph nodal (L.N.) involvement in patients with clinically localized prostate cancer. Its positive predictive value (PPV), negative predictive value (NPV), and accuracy are superior to that of current nomograms in use. Use of this method can result in enormous cost savings by accurately diagnosing patients with prostate cancer and by avoiding multiple imaging tests and expensive surgery in unindicated patients.

The subject invention provides a method which is very accurate in identifing patients with margin positive disease, L.N., and S.V. involvement. Specifically, it has been determined that the application of the method of the subject invention will miss only 14% of patients with margin positive disease, 2% with L.N., and 0% with S.V. involvement and will preclude unnecessary staging tests in 63% of patients. Significant cost savings can thus be achieved using the methods of the subject invention.

The subject invention is generally a method for evaluating the stage of prostate cancer in a patient using a neural network. The neural network provides prostate cancer stage information for the patient based upon input data such as the patient's preoperative serum PSA, biopsy Gleason score, and systemic biopsy-based information. The neural network must first be trained by clinical testing of a test population of patients with prostate cancer to obtain teaching data for the network (such as preoperative serum PSA, biopsy Gleason score, and systemic biopsy-based information). The network then automatically calculates secondary data based on the teaching data for normalization of the inputs. The teaching data and the secondary data are input into the neural network, so that the neural network can be trained to provide an output variable corresponding to the stage of prostate cancer. The output variables include margin positivity, seminal vesicle involvement, and lymph nodal involvement. The network may be trained to provide other output variables as desired.

For each of the output variables, specific secondary input data is calculated automatically by the neural network to normalize the inputs. For example, for the margin positivity output variable, secondary input data preferably includes one or more of race code, DRE code, a PSA to age ratio, log of PSA, TRUS code, a log of biopsy weighted PSA, a bilateral or greater than 2 on biopsy, a bilateral cancer on biopsy, a cancer greater than 2 cores on biopsy, perineural infiltration, a log Gleason weighted PSA, and a biopsy Gleason. For the seminal vesicle involvement output variable, secondary input data preferably includes one or more of log biopsy weighted PSA, log Gleason weighted PSA and biopsy Gleason. For the lymph nodal involvement output variable, secondary input data preferably includes one or more of race code, PSA/age ratio, TRUS code, log biopsy weighted PSA, log Gleason weighted PSA, and biopsy Gleason.

The subject invention also includes a method for developing an appropriate treatment plan for a patient with prostate cancer by providing input data to the trained neural network. The input data includes the patient's preoperative serum PSA, biopsy Gleason score, and systemic biopsy-based information, as well as any secondary data calculated by the network. The output information provided by the neural network is utilized to formulate the treatment plan.

The subject invention also includes a system, in addition to the above-described method, for diagnosing prostate cancer in a patient which uses a neural network. The neural network first receives as input specific primary teaching data obtained from clinical testing of a test population of patients with prostate cancer and then calculates secondary teaching data based on the primary teaching data. The neural network learns the teaching data and is thereafter trained to provide an output variable for a pathological feature in question. When the neural network then receives primary patient input data obtained from clinical testing of a patient to be diagnosed, it calculates secondary patient input data based on the primary patient input data, and the neural network then provides the output variable for diagnosis of the pathological feature in question for the patient.

The method for diagnosing prostate cancer in a patient of the subject invention, in an alternate embodiment, includes the steps of: a) selecting certain clinical parameters for a pathological feature in question; b) converting these clinical parameters into numerical expressions; c) inputting the numerical expressions into a neural network to train the neural network to provide an output variable for the pathological feature in question; d) obtaining from a patient the necessary clinical parameters; e) converting the clinical parameters into numerical expressions; and f) inputting the numerical expressions into the neural network to obtain the output variable for diagnosing prostate cancer in the patient.

In another embodiment, the method for diagnosing prostate cancer in a patient includes the steps of: a) clinical testing of a test population of patients with prostate cancer to obtain primary teaching data; b) calculating secondary teaching data based on the primary teaching data; c) inputting the primary and secondary teaching data into a neural network for use in diagnosing patients and causing the neural network to learn the teaching data, so that the neural network is trained to provide an output variable for a pathological feature in question; d) clinical testing of patient to be diagnosed to obtain primary patient input data; e) calculating secondary patient input data based on the primary patient input data; f) inputting the primary and secondary patient input data into the neural network; and g) obtaining a diagnosis for the pathological feature in question for the patient from the output variable of the neural network.

In yet another embodiment of the subject invention, a method for diagnosing prostate cancer in a patient utilizing a trained neural network is provided. In this method, the neural network is already trained by clinical testing of a test population of patients with prostate cancer to obtain primary teaching data; calculating secondary teaching data based on the primary teaching data; and inputting the primary and secondary teaching data into a neural network to train it to provide an output variable for a pathological feature in question. This method includes the steps of: a) clinical testing of patient to be diagnosed to obtain primary patient input data; b) calculating secondary patient input data based on the primary patient input data; c) inputting the primary and secondary patient input data into the neural network; and d) obtaining a diagnosis for the pathological feature in question for the patient from the output variable of the neural network. The primary patient input data preferably includes preoperative serum PSA, biopsy Gleason score, and systemic biopsy-based information. The output variables preferably include margin positivity, seminal vesicle involvement, and lymph nodal involvement. The method further includes the step of applying smoothing factors to the input data. The output variable may be provided as binary probability predictions or continuous probability predictions.

The subject invention also includes a method for training a neural network for diagnosing prostate cancer in a patient including the steps of: a) clinical testing of a test population of patients with prostate cancer to obtain primary teaching data, the primary teaching data comprising preoperative serum PSA, biopsy Gleason score, and systemic biopsy-based information; b) calculating secondary teaching data based on the primary teaching data; and c) inputting the primary and secondary teaching data into a neural network for use in diagnosing patients and causing the neural network to learn the teaching data, so that the neural network is trained to provide an output variable for a pathological feature in question. The secondary teaching data includes ratios and logarithms of the primary teaching data and the primary patient input data respectively. The secondary teaching data may be selected from one or more of a log 10 of the serum PSA, a weighting of the PSA, a ratio of the PSA and the biopsy-based information, a ratio of the PSA with the Gleason score, and an aggressive or non-aggressive factor based on the PSA, the Gleason score and the biopsy-based information. The neural network is preferably a probabilistic three-layer neural network possessing an input layer, a hidden layer, and an output layer, based on Bayesian theory which separates data into a specified number of output categories. The neural network is preferably trained based on genetic adaptive algorithms using calibration to testing smoothing factors as individual multipliers for each of the input data. The continuous probability predictions are preferably subjected to nonparametric receiver-operator characteristic curve (ROC) analysis. Test patients unable to undergo TRUS-guided biopsy, had preoperative hormonal radiation, or cryotherapy, or did not undergo pelvic lymphadenectomy are usually excluded.

DETAILED DISCLOSURE OF THE INVENTION

Figure 1:
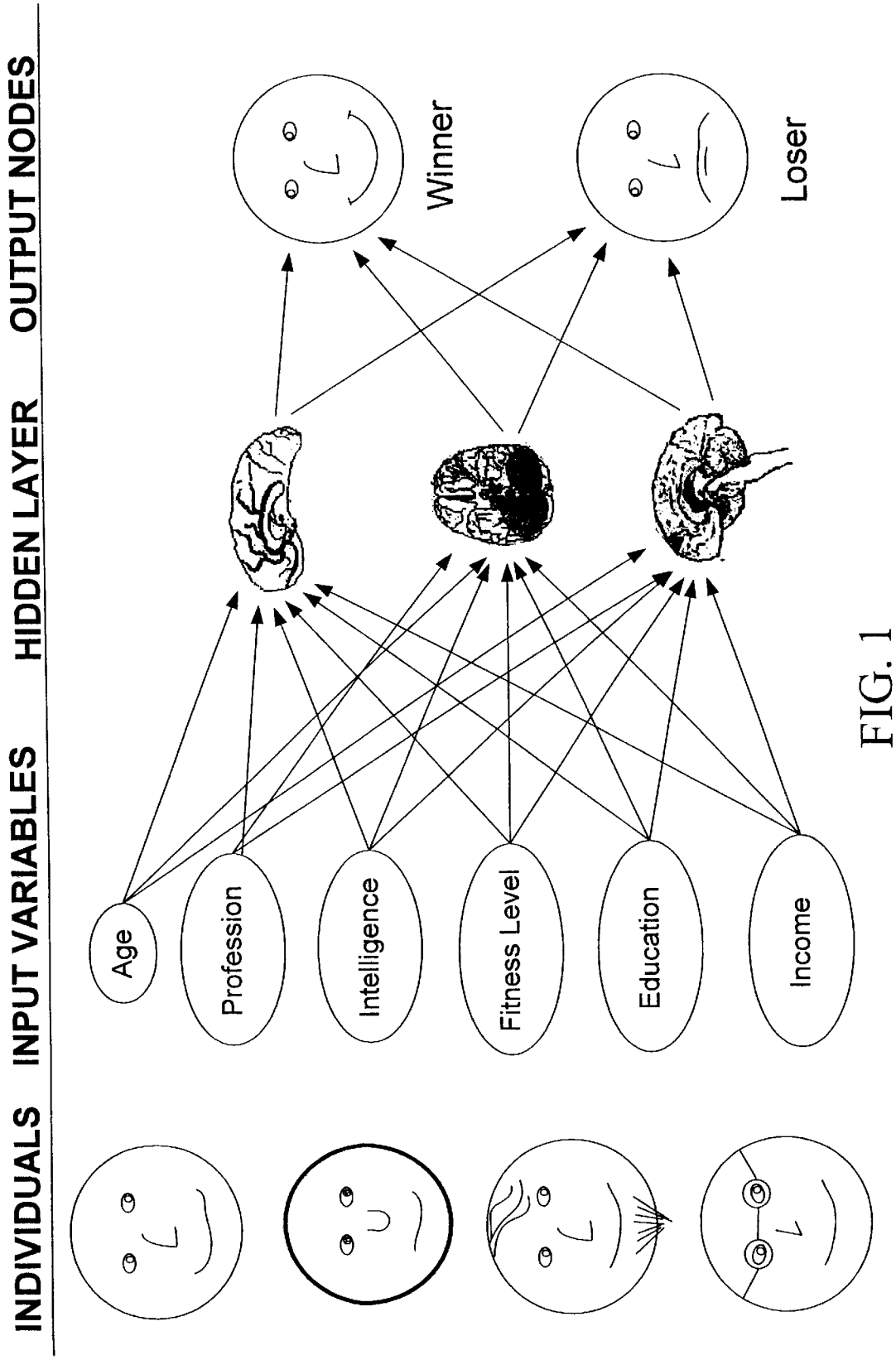
FIG. 1. Diagrarmmatic representation of PNN showing input variables, nodal structure, and output categories.

Using the teachings provided herein, it is possible to construct, train, test, and utilize a neural network for screening of prostate cancer and for clinical staging of prostate cancer. Generally, the steps involved in training the network include clinical testing of a test population of patients with prostate cancer to obtain teaching data for the neural network. This teaching data includes, for example, primary inputs of preoperative serum PSA, biopsy Gleason score, and systemic biopsy-based information (e.g., clinical staging). Secondary teaching data, based on these primary inputs, is automatically calculated and is also input into the neural network to simplify recognition of trends in the data by the neural network. This secondary teaching data includes, for example, ratios and logarithms of the primary teaching data such as log PSA, weighted PSA, PSA/extent ratio, PSA/Gleason ratio, and aggressive vs. nonaggressive factor based on PSA, Gleason and extent. The output variables of the neural network include, for example, margin positivity, seminal vesicle involvement, and lymph nodal involvement. The network may be trained to provide other output variables as desired.

For each of these output variables, specific data is input into the neural network during training. For example, when output variables with respect to margin positivity are desired, the teaching data (primary and secondary) preferably comprises at least one of twelve (12) inputs, namely, race code, DRE code, PSA/age ratio, Log PSA, TRUS code, Log biopsy weighted PSA, bilateral or >2 on biopsy, bilateral cancer on biopsy, cancer >2 cores on biopsy, perineural infiltration, log Gleason weighted PSA and biopsy Gleason. An individual smoothing factor (multiplier) may be applied to each of these inputs as determined by the genetic adaptive algorithm of the neural network. Similarly, when output variables with respect to seminal vesicle involvement are desired, the teaching data preferably comprises at least one of three inputs, namely, log biopsy weighted PSA, log Gleason weighted PSA and biopsy Gleason. Smoothing factors are again appropriately applied. Finally, when output variables with respect to lymph nodal involvement are desired, the teaching data preferably comprises at least one of six inputs, namely, race code, PSA/age ratio, TRUS code, log biopsy weighted PSA, log Gleason weighted PSA, and biopsy Gleason. Based on this teaching data, the neural network is trained to provide an output variable for a pathological feature in question.

Once trained, specific patient data obtained during clinical testing of the patient is input into the neural network to obtain a specified output variable. The neural network automatically calculates secondary patient input data to be input into the neural network which includes ratios and logarithms of the primary patient input data such as log PSA, weighted PSA, PSA/extent ratio, PSA/Gleason ratio, and aggressive vs. nonaggressive factor based on PSA, Gleason and extent. The output variables of the neural network for a specific patient may include, for example, margin positivity, seminal vesicle involvement, and lymph nodal involvement.

In order to train, test and validate the neural network according to the subject invention, approximately one thousand patients of clinically organ confined prostate cancer underwent preoperative staging using serum prostate specific antigen (PSA), needle biopsy based staging, and Gleason scoring prior to radical prostatectomy and lymph node dissection. The performance of the network of the subject invention was validated in a subset of patients and network predictions were compared with actual pathological stage. During this training, the mean age was 62.9 years, mean serum PSA was 8.1 ng/ml, and mean biopsy Gleason score was six. Overall 55% of patients had organ-confined disease, 27% had positive margins, 8% had seminal vesicle involvement, and 7% had lymph nodal disease. Thirty percent of margin positive patients also had additional SV involvement while 50% of SV positive patients also had positive margins.

The sensitivity of our method ranged from 76–100%, and specificity ranged from 64–72% for various predictions (output variables) of margin positivity, S.V., and L.N. involvement. The negative predictive values (NPV) tended to be relatively high for all features considered (86–100%), while positive predictive values (PPV) tended to be relatively low. Due to the significantly high negative predictive value and low positive predictive value, this staging modality can be quite useful in screening patients and in initial staging. Further testing can be avoided in about 63% or more of patients with organ confined cancer. By using this approach, it is expected that only about 37% or less of all patients will need further testing for extraprostatic disease, seminal vesicle disease, and lymph node spread.

Neural Networks
Fundamentals of parallel processing

The neural network contains a large number of simple neuron-like processing elements and large number of weighted connections between the elements. The weights on the connections encode the knowledge of a network. Despite their diversity, all artificial intelligence neural networks perform essentially the same function-they accept a set of inputs (an input vector) and process it in the intermediate (hidden) layer of processors (neurons) by an operation called vector mapping (FIG. 1). Each neuron in a processor unit receives inputs from one or many neurons of previous layers. The aggregate of these inputs will be processed by the neuron, and input will either be passed on to the next layer or will be aborted. The next layer may be an additional layer of hidden neurons or output neurons. The topology of neuronal connections between various layers of neural network (input, hidden, and output) varies in terms of interconnection schema (feed forward, or recurrent connections). In summary, the output neuron will either fire or not fire depending upon the following factors: number of inputs, weight of inputs, process of inputs in each neuron (activation connectors), and number of hidden layer neurons.

Network properties

The topology of a neural network refers to its framework and its interconnection scheme. The framework is often described by the number of layers, and number of nodes per layer. According to the interconnection schema, a network can be either feed forward (all connection points in one direction) or recurrent (with feedback connections and loops). The connections can either be symmetrical (equally weighted directional) or asymmetrical.

The high-order connection is the one that combines the inputs from more than one node, often by multiplication. The numbers of the inputs determines the order of connection. The order of neural network is the order of the highest order connection. The connection weights can be real numbers or integers. They are adjustable during network training, but some can be fixed deliberately. When training is completed, all of them are fixed.

Node properties

The activation levels of nodes can be discrete (e.g., 0 and 1), continuous across a range (e.g., [0,1]), or unrestricted. The activation (transfer) function can be linear, logistic, or sigmoid.

System dynamics

The weight initialization scheme is specific to the particular network model chosen. However, in many cases initial weights are just randomized to small numbers. The learning rule is one of the most important attributes to specify for a neural network. The learning rule determines how to adapt connection weight in order to optimize the network performance. It additionally indicates how to calculate the weight adjustments during each training cycle. The inference behavior of a neural network is determined by computation of activation level across the network. The actual activation levels necessary are determined to calculate the errors which are then used as the basis for weight adjustments.

Learning

Artificial neural networks learn from experience. The learning methods may broadly be grouped as supervised or unsupervised. Many minor variations of such paradigms exist. Supervised learning: The network is trained on a training set consisting of vector pairs. One vector is applied to the input of the network; the other is used as a "target" representing the desired output. Training is accomplished by adjusting the network weights so as to minimize the difference between the desired and actual network outputs. This process is usually an iterative procedure in which the network output is compared to the largest vectors. This produces an error signal which is then used to modify the network weights. The weight correction may be general (applied to entire network) or specific (to that individual neuron). In either case, the adjustment is in a direction that reduces the error. Vectors from the training set are applied to the network repeatedly until the error is at an acceptably low level. Unsupervised learning (self-organization): It requires only input vectors to train the network. During the training process, the weights are adjusted so that similar inputs produce similar outputs. In this type of network, the training algorithm extracts statistical regularities from the training set, representing them as the value of network weights.

Generalization

The real-world problems lack consistency; two experiences are seldom identical in every detail. For a neural network to be useful, it must accommodate this variability, producing the correct output despite insignificant deviations between the input and test vector. This ability is called generalization.

Classification

This is a special case of vector mappings which has a broad range of applications. Here, the network operates to assign each input vector to a category. A classification is implemented by modifying a general vector mapping network to produce mutually exclusive primary outputs.

Genetic algorithms

This is a novel means of training the neural networks. Network learning is based upon genetic mechanisms of evolution which result in survival and genesis of intelligent, self-organizing, self-repairing, self-motivating organisms which are strongest among the pool of individuals and genetic patterns. These algorithms emulate the process of natural selection and survival of the fittest. This involves searching high-dimensional spaces for superior solutions. The algorithms are simple, robust, and general; no knowledge of the search space is assumed. They are based on principles of parallel processing. Conventional optimization techniques are based upon adjusting the parameters of a model to produce a desired result. For example, training an artificial neural network involves modifying its weights so that it produces the desired relationship between inputs and outputs. Genetic algorithms, on the other hand, optimize the performance based on biological genetics and natural selection. This involves maintenance and modification of the characteristics of a population of solutions (individuals) over a large number of generations. This results in production of successive populations having an increasing number of individuals with desirable features by maximizing the probability of proliferation of those individuals who exhibit them.

Genetic algorithm operates on coded parameters, rather than the raw parameters. This is quite like the strand of DNA which encodes all of the characteristics of a human in chains of amino acids, so the parameters of the problem must be encoded in final length strings. Optimization is performed on a set of strings where each string is composed of a sequence of characters. Given an initial population of strings, a genetic algorithm produces a new population of strings according to a set of genetic rules. This constitutes one generation. The rules are devised so that the new generation tends to have strings that are superior to those in previous generations, measured by some objective function. Successive generations are thus better than previous ones. Optimizing a population rather than a single individual contributes to the robustness of these algorithms.

Definitions

Estimated Sensitivity: proportion of patients with the feature of interest who were correctly classified by the neural net.

Estimated Specificity: proportion of patients without the feature of interest who were correctly classified by the neural net.

Estimated Positive Predictive Value: proportion of patients classified by the neural net as positive for the feature who in fact had the feature.

Estimated Negative Predictive Value: proportion of patients classified by the neural net as negative for the feature who in fact did not have the feature.

Materials and Methods

Patients and preoperative evaluation

The study population consisted of 1000 patients with prostate cancer. The patients were drawn from three university hospitals, two VA medical centers, a large HMO practice, and the private practices of three prominent area urologic oncologists. All patients underwent pelvic lymphadenectomy and radical prostatectomy. Preoperatively, all patients underwent three or more biopsies from each lobe of the prostate under ultrasound guidance in addition to lesion directed biopsy if any suspicious areas were noted. The seminal vesicles (S.V.) were biopsied if there was any suspicion of involvement. The criteria for S.V. biopsy was similar to that described by Ohori and associates (Ohori, M., S. Egawa, K. Shinohara et al. [1994] Br. J. Urol. 74:72–79; Ohori, M., K. Shinohara, T. M. Wheeler et al. [1993] Br. J. Urol. 72:799–808; Ohori, M., P. T. Scardino, S. L. Lapin et al. [1993] Am. J. Surg. Pathol. 17:1252–1261).

All patients underwent serum PSA estimation prior to biopsy using "TANDEM-R" two-site radioimmunoassay (Hybritech (R) Inc., San Diego, Calif.). The highest serum PSA was used in the analyses.

Assessment of Clinical Extent of Cancer

Based on the biopsy results, patients were classified as having T1a if the cancer was diagnosed on TURP and occupied <5% of tissue; T1b if diagnosed incidentally and occupied >5% of tissue; T1c when diagnosed only on the basis of elevated PSA; T2a–b (B1) disease if the biopsies showed one lobe positive, T2c (B2) disease if the biopsies from both lobes were positive, and T3 (C) disease if extracapsular extension (ECE) was documented or if the S.V. biopsy was positive for prostate cancer. Biopsy findings were reported using a Gleason grading system. The highest biopsy score was assigned to each patient if the field contained more than one Gleason score (Ohori, M., T. M. Wheeler, P. T. Scardino [1994] Cancer 74:104–114; Narayan et al., supra; Chisholm, G. D., P. O. Hedlund, J. Adolfsson et al. [1994] Scand. J. Urol. Nephrol Suppl. 162:107–114).

Exclusion criteria

Patients were excluded from the study if they were unable to undergo TRUS-guided biopsy, if they had preoperative hormonal, radiation, or cryotherapy, or if they did not undergo pelvic lymphadenectomy.

Operative protocol

Radical retropubic prostatectomy was performed in all patients using the standard technique described by Dr. Walsh (Brendler, C. B., P. C. Walsh [1992] CA Cancer J. Clin. 42:212–222). Nerve sparing prostatectomy was reserved for patients with unilateral cancers.

Histopathology

Frozen section analyses of lymph nodes were performed based on the discretion of the operating surgeon. In the vast majority of patients, frozen section was performed only in patients who had clinically suspicious nodes. If the lymph nodes were positive on frozen section biopsy, radical prostatectomy was abandoned. All lymph node samples were further subjected to permanent section. After removal, specimens were coated with India ink, weighed, and measured in the anteroposterior, cephalocaudal, and transverse dimensions. Prostates were embedded in their entirety and fixed in 10% formalin for 18 to 24 hours. After fixation, the distal and proximal urethral margins were removed for histological examination. The prostate and seminal vesicles were step-sectioned at 3–5 mm intervals perpendicular to the long axis of the gland, and each section was examined histologically. Pathologic stage was reported as organ confined, extracapsular penetration with or without positive surgical margins, seminal vesicle involvement, and/or involvement of lymph nodes. Gleason score was assigned based on the area of the most aggressive cancer.

Probability Nomograms: Testing of Accuracy

The nomograms were used as described in original articles (Partin et al., supra; Parin and Walsh, supra; Narayan et al., supra). The accuracy of these plots was calculated in 100 patients by using a probability cutoff point of greater than 15–20% in defining margin positivity, and cutoff points of greater than 5% probability in defining S.V. and L.N. positivity. The sensitivity, accuracy, positive predictive, and negative predictive values were calculated based on standard statistical methods as described herein. These cutoffs were used on the basis of clinical judgment and percentages which most clinicians use during preoperative counseling with the patient.

Neural network architecture used in our study

The data was collected in a spreadsheet on an IBM compatible personal computer. Standard statistical explorations to computer mean, median and standard deviations were conducted. Based on the need to classify the noisy clinical data into groups, several neural network architectures were explored to determine the appropriateness of a prediction model. After experimenting with several simpler backpropagation networks, a probabilistic neural network was chosen for the subject invention. Probabilistic neural networks (PNN) are based on Bayes decision theorem and nonparametric statistics to calculate the probability density function. These networks learn pattern statistics from a training set (teaching data). The training may be in terms of global or local basis functions. The global basis function is defined as nonlinear (usually sigtnoidal) functions of the distance of the pattern vector from a hyperplane. The function to be approximated is defined as a combination of these sigmoidal functions. The PNN learns in two ways, basic and adaptive forms. The basic forms are characterized by one pass learning and the use of the same width for the basis function for all dimensions of the measurement space. Adaptive PNNs on the other hand are characterized by adapting separate widths for the basis function for each dimension. Because this adaptation is iterative, it sacrifices the one pass learning in the basic forms, but it achieves better generalization accuracy then the basic forms.

The probabilistic Neural Network (PNN) separates data into a specified number of output categories. PNNs are a type of supervised network, based on Bayesian theory, and are essentially three-layered networks. In this network, the training patterns are presented to the input layer, and the output layer has one neuron for each possible category. There must be as many neurons in the hidden layer as there are training patterns. The network produces activations in the output layer corresponding to the probability density function estimate for that category. The highest output represents the most probable category. PNNs are known for their ability to train quickly on sparse data sets and separate data into a specified number of output categories.

PNN Training Criteria

Distance metric: PNN networks work by comparing patterns based upon their distance from each other. We used Vanilla Euclidean distance metric because it worked best for our data (Niederberger et al. [1993] supra; Fu [1994] supra).

Calibration for PNNs

Determination of smoothing factor: We tested hundreds of combinations for margin positivity, S.V. disease, and L.N. metastasis separately until we found the best combination of weights and smoothing factors for each event.

Genetic adaptive

We used a genetic algorithm to find appropriate individual smoothing factors for each input as well as an overall smoothing factor (the input smoothing factor is an adjustment used to modify the overall smoothing factor to provide a new value for each input) (Niederberger et al. [1993] supra; Fu [1994] supra).

Training algorithm

Training using a genetic adaptive algorithm proceeds in two parts. The first part trains the network with the data in the training set. The second part uses calibration to test a whole range of smoothing factors, trying to home in on one combination that works best for the test set with the network created in the first part. The genetic algorithm is looking for a smoothing factor multiplier for each input, which in essence is an individual smoothing factor for each input (Niederberger et al. [1993] supra; Fu [1994] supra).

At the end of training, the individual smoothing factors may be used as a sensitivity analysis tool in which the larger the factor for a given input, the more important that input is to the model at least as far as the test set is concerned. Inputs with low smoothing factors are candidates for removal at a later trial, especially if the smoothing factor gets set to zero.

Training, Testing, and Validation

Out of 1000 patients, we used 50–60% for training, 30–40% for testing, and 10–20% as production set for validation. These sets were selected on the basis of random numbers generated by the computer. During training, the network calculated the best smoothing factor and tested its performance against the test set data. Over-training of the network was avoided by calculating the RMS error after every generation. The accuracy of the network was assessed on the basis of its performance with the production set. The validation set data (production set) was never seen by the neural network. Based on the input variables (see result section), the network classified the output variable as positive or negative for the pathological feature in question. The output variables used in this study include margin positivity, seminal vesicle involvement, and lymph nodal disease. Network output was then compared with actual pathological stage of that individual patient, and results were grouped as right or wrong. The accuracy, sensitivity, specificity, and positive and negative predictive values were then calculated on this production set.

Variable Selection

The following preoperative information was used for neural network training: race, age, rectal examination findings, size of tumor on ultrasound, serum PSA, biopsy Gleason, systemic biopsy based staging information such as bilaterality of cancer and number of positive cores (out of 6) and perineural infiltration data. Output variables were as follows: margin positivity, seminal vesicle positivity and lymph node positivity.

Statistical Methods in Assessing Diagnostic Performance of Neural Net Predictions of Prostate Pathology The data were collected on "EXCEL(R)" (Microsoft Corporation, Redmond, Wash.) computer software for PC. A 120 MHZ "PENTIUM(R)" (Intel Corp., Santa Clara, Calif.) PC from Gateway 2000 (North Sioux City, S. Dak.) with 32 MB RAM and 1 gigabyte hard drive was used for network training. It took about 12–14 hours for training in a genetic breeding pool of 300 patients. The network was written in "WINDOWS" based computer language.

For each pathological feature of interest, a trained neural network algorithm was used to generate both binary probability predictions (based on Bayesian theorem; p=0 or 1) and continuous probability predictions regarding the presence of the feature in each patient within a group of patients of known status (i.e., positive or negative for the feature). Diagnostic performance summary statistics (sensitivity, specificity, sample-specific positive and negative predictive values, and overall percent of patients correctly classified) were computed for the binary predictions along with one-tailed lower 95% confidence bounds for sensitivity and specificity.

The continuous probability predictions were subjected to nonparametric receiver-operator characteristic curve (ROC) analysis. This involved the use of a unique predicted probability as a cut point for classifying patients as either highly likely or highly unlikely to have the feature of interest. Diagnostic performance summary statistics were computed for each of the probability cut points. Cut points associated with the highest sensitivity observed at unique corresponding levels of specificity and the highest specificity observed at unique corresponding levels of sensitivity were used to construct tables of summary statistics and ROC curves of specificity versus sensitivity. The rank correlation statistic generated by the SAS procedure PROC LOGISTIC was used to estimate the are under the observed ROC curve. The area under the curve (AUC), expressed as a proportion of the area under the ROC curve of a perfectly performing predictor, can be considered a relative measure of information content provided by a separation and overlap of predicted probabilities associated with the actual presence or absence of a feature of interest. In Tukey box plots, the white bar inside the box indicates the 50th percentile (median) of the distribution of predicted probabilities. The upper and lower ends of the box indicate the 25th and 75th percentiles of the distribution. The span between these percentiles is known as the inter-quartile range. Whiskers extending from either end of the box are drawn to the furthest data points still within two box lengths from the middle of the box. Points beyond those limits are marked individually and typically considered extreme values in the context of the displayed distribution. The performance of the network based prediction (based on Bayesian theorem) was then compared with the performance of ROC area under the curve for linear output.

Following are examples which illustrate procedures for practicing the invention. These examples should not be construed as limiting. All percentages are by weight and all solvent mixture proportions are by volume unless otherwise noted.

Specific Example 1—Training the Neural Network

Step 1. Clinical Testing

Clinical testing of a test population (1000) of patients with prostate cancer to obtain teaching data for the neural network. Each patient was classified (clinical staging) as having T1a if the cancer was diagnosed on TURP and occupied <5% of tissue; T1b if diagnosed incidentally and occupied >5% of tissue; T1c when diagnosed only on the basis of elevated PSA; T2a–b (B1) disease if the biopsies showed one lobe positive, T2c (B2) disease if the biopsies from both lobes were positive, and T3 (C) disease if extracapsular extension (ECE) was documented or if the S.V. biopsy was positive for prostate cancer. Table 1 summarizes the prevalence of these various clinical stages of prostate cancer and corresponding pathological features. In our study, 56% of patients had organ-confined disease, 28% had positive margins, 8% had seminal vesicle involvement, and 9% had lymph node disease.

TABLE 1

Overall prevalence of various clinical stages and pathological features in entire data set

| Clinical stage | # Patients | Organ-confined | Margin+ | Seminal vesicle+ | Lymph node+ |
|---|---|---|---|---|---|
| T1a | 10 | 9 | 1 | 0 | 0 |
| T1b | 18 | 14 | 1 | 1 | 2 |
| T1c | 86 | 44 | 26 | 0 | 4 |
| T2a–2b | 665 | 373 | 159 | 53 | 19 |
| T2c | 131 | 64 | 51 | 11 | 21 |
| T3 | 90 | 56 | 40 | 12 | 7 |
| Total | 1000 | 560 (56) | 178 (28) | 77 (8) | 85 (9) |

ECE = extracapsular extension
S.V. = seminal vesicle

Step 2. Construction and Training of Neural Network

Once the teaching data was obtained from the test population, (e.g., preoperative serum PSA, biopsy Gleason score, and systemic biopsy-based information for each of the test patients), secondary teaching data, based on these primary inputs, was calculated to simplify recognition of trends in the data by the neural network. This secondary teaching data comprised various ratios and logarithms of the primary teaching data. Table 2 summarizes these various teaching input variables used for construction and training of the neural network. The three primary teaching inputs were preoperative serum PSA, biopsy Gleason score, and systemic biopsy-based clinical staging. The other secondary input variables were simply the combination of these three primary variables, their logarithms, and their ratios. Based on this teaching data, the neural network was trained to provide an output variable for a pathological feature in question. The output variables of the neural network included margin positivity, seminal vesicle involvement, and lymph nodal involvement.

TABLE 2

Various input variables for neural network

| S.N. | Input variable | Comment |
|---|---|---|
| 1. | Serum PSA | Pre-biopsy serum prostate-specific antigen in ng/ml |
| 2. | *Log PSA | Log 10 of serum PSA |
| 3. | *Weighted PSA | Serum PSA<10:0;>11:1 |
| 4. | Clinical extent | 1: Organ-confined and unilateral; 2: Organ-confined and bilateral; 3: ECE suspected; 4: Seminal vesicle involvement suspected |
| 5. | Biopsy Gleason score | 2–10 |
| 6. | *PSA/Extent | Ratio of PSA and Extent |
| 7. | *PSA/Gleason | Ratio of PSA with Gleason |
| 8. | *Aggressive vs. non-aggressive | Non-aggressive: PSA<10, Gleason<6, and Extent: 1 & 2; Aggressive: PSA>10, Gleason 8 or more, and Extent: clinical suspicion for non-organ-confined disease |

*Various ratios were calculated, and substratifications done to simplify recognition of trends in the data by Neural Network.

Detailed results of our studies are provided in the following Tables 3–5 and FIGS. 2a–4b. The estimates of sensitivity and specificity for binary predictions by PNNs tended to be slightly better than optimal cut point estimates of sensitivity and specificity using ROC curves for continuous probability predictions. Sample-specific negative predictive values (NPV) tended to be relatively high for all features considered (86–100%). Sample-specific positive predictive values (PPV) tended to be relatively low, particularly for lymph nodes (19%) and seminal vesicles (13%).

a. Margin Positivity Results

Figure 2A:
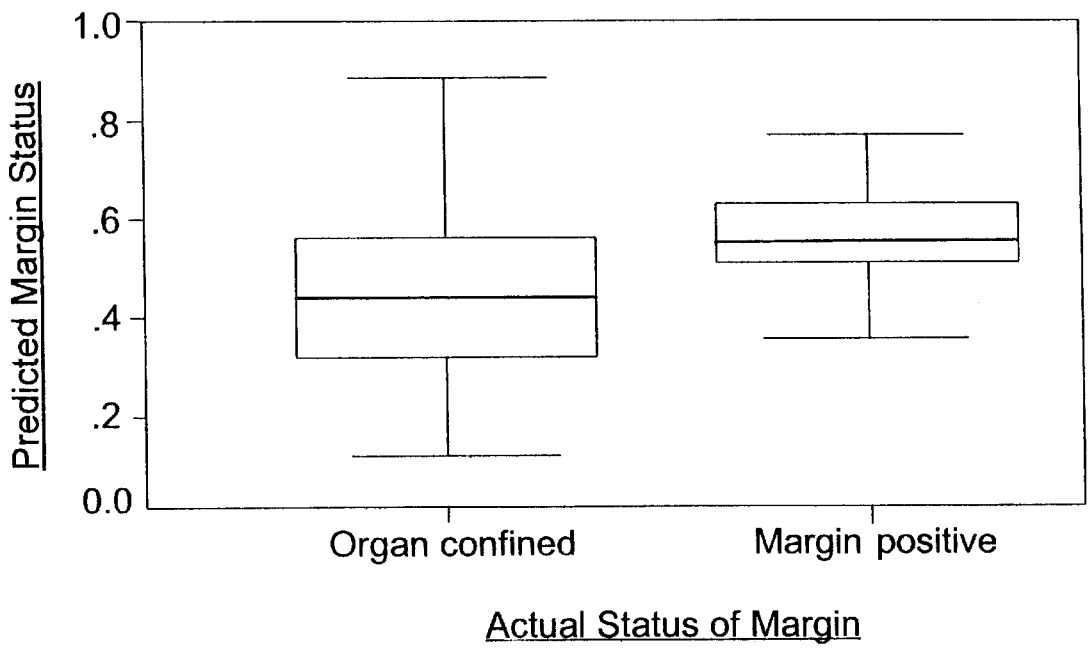
FIGS. 2a–2b. Box plot and ROC analysis of network output (continuous) for margin positivity. The accuracy was always better by Bayesian theorem analysis.
Figure 2B:
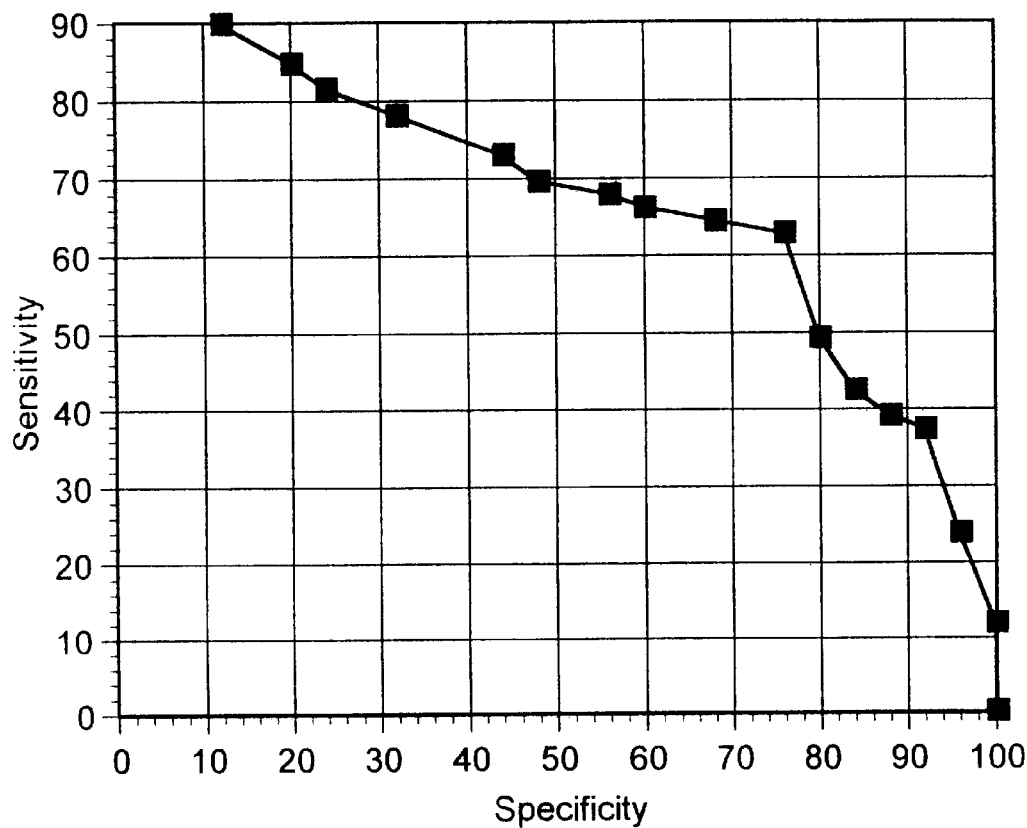

Results with respect to margin positivity can be seen in Table 3 and FIGS. 2a–2b.

TABLE 3

Neural net predicted probabilities (Bayesian theorem) of margin positivity vs. ROC prediction of network output ("O-1" indicates neural net binary prediction) in production set

| Cutoffs Probability Level | Positive patients Neural Net Right | Neural Net Wrong | Negative patients Neural Net Right | Neural Net Wrong | Overall Accuracy | Accuracy percentages Sensitivity | Specificity | PPV | NPV |
|---|---|---|---|---|---|---|---|---|---|
| 0.000 | 25 | 0 | 0 | 59 | 29.8 | 100.0 | 0.0 | 29.8 | — |
| 0.272 | 25 | 0 | 7 | 52 | 38.1 | 100.0 | 11.9 | 32.5 | 100.0 |
| 0.311 | 24 | 1 | 14 | 45 | 45.2 | 96.0 | 23.7 | 34.8 | 93.3 |
| 0.358 | 23 | 2 | 22 | 37 | 53.6 | 92.0 | 37.3 | 38.3 | 91.7 |
| 0.372 | 22 | 3 | 23 | 36 | 53.6 | 88.0 | 39.0 | 37.9 | 88.5 |
| 0.384 | 21 | 4 | 25 | 34 | 54.8 | 84.0 | 42.4 | 38.2 | 86.2 |
| 0.432 | 20 | 5 | 29 | 30 | 58.3 | 80.0 | 49.2 | 40.0 | 85.3 |
| 0.482 | 19 | 6 | 37 | 22 | 66.7 | 76.0 | 62.7 | 46.3 | 86.0 |
| 0.507 | 17 | 8 | 38 | 21 | 65.5 | 68.0 | 64.4 | 44.7 | 82.6 |
| 0.519 | 15 | 10 | 39 | 20 | 64.3 | 60.0 | 66.1 | 42.9 | 79.6 |
| 0.530 | 14 | 11 | 40 | 19 | 64.3 | 56.0 | 67.8 | 42.4 | 78.8 |
| 0.535 | 12 | 13 | 41 | 18 | 63.1 | 48.0 | 69.5 | 40.0 | 75.9 |
| 0.545 | 11 | 14 | 43 | 16 | 64.3 | 44.0 | 72.9 | 40.7 | 75.4 |
| 0.574 | 8 | 17 | 46 | 13 | 64.3 | 32.0 | 78.0 | 38.1 | 73.0 |
| 0.612 | 6 | 19 | 48 | 11 | 64.3 | 24.0 | 81.4 | 35.3 | 71.6 |
| 0.629 | 5 | 20 | 50 | 9 | 65.5 | 20.0 | 84.7 | 35.7 | 71.4 |
| 0.716 | 3 | 22 | 53 | 6 | 66.7 | 12.0 | 89.8 | 33.3 | 70.7 |
| 1.000 | 0 | 25 | 59 | 0 | 70.2 | 0.0 | 100.0 | — | 70.2 |
| ROC: 0-1 | | Lower 95% Bound: | | | 58.5 | 58.1 | 52.9 | 33.8 | 74.9 |
| PNN 0/1 | 19 | 6 | 38 | 21 | 67.9 | 76.0 | 64.4 | 47.5 | 86.4 |

Sample specific prevalence of positive margin - 25/84 = 29.8%
ROC: Receiver operator curves
PNN: Probabilistic Neural Network
Area under the curve (AUC): .701

Prevalence of margin positivity in the sample was 29.8%. Neural net sensitivity and specificity for this feature were 76.0% and 64.4%, respectively, with corresponding 95% lower confidence bounds of 58.1% and 52.9%. Sample-specific positive and negative predictive values were 47.5% and 86.4%, respectively, with corresponding 95% lower confidence bounds of 33.8% and 74.9%.

Due to better negative predictive value (86%), less than 15% of patients labeled as negative actually had margin positive disease. In our data set approximately 52% (44/84) of all patients were actually labeled negative by the network, and its prediction was wrong in <15% of the patients. There were 48% (40/84) of patients who were labeled positive and only 52.5% (PPV=48%) of these actually had margin positive disease. Therefore, the utility of the network in 48% (labeled positive) of patients was not very useful. However, the high negative predictive value allows it to be an excellent initial staging tool which can preclude any additional testing in approximately 52% of patients who can directly proceed for definitive radical therapy.

Parameters of interest (e.g., input variables, smoothing factors) in this analysis are provided in Table 4. Specifically, for margin positivity, the teaching data (primary and secondary) preferably comprises at least one of twelve (12) inputs, namely, race code, DRE code, PSA/age ratio, Log PSA, TRUS code, Log biopsy weighted PSA, bilateral or >2 on biopsy, bilateral cancer on biopsy, cancer >2 cores on biopsy, perineural infiltration, log Gleason weighted PSA and biopsy Gleason. An individual smoothing factor (multiplier) was applied to each of these inputs as determined by the genetic adaptive algorithm of the neural network.

TABLE 4

| Network type | PNN, genetic adaptive |
|---|---|
| Problem name | C:\STAGENET\MARGNET\MARGNET |
| Number of inputs | 12 |
| Number of outputs | 2 |
| Number of training patterns | 134 |
| Number of test patterns smoothing test individuals | 134 |
| current best smoothing factor | 1.0 |
| smoothing test generations | 97 |
| last number incorrect | 11.00106 |
| minimum number incorrect | 11.00099 |
| generations since min. incorrect | 21 |

| Input # | Input name | Individual smoothing factor |
|---|---|---|
| 1 | Race Code | 0.27059 |
| 2 | DRE Code | 0.02353 |
| 3 | PSA/Age Ratio | 1.62353 |
| 4 | Log PSA | 0.01176 |
| 5 | TRUS Code | 2.65882 |
| 6 | Log Biopsy Weighted PSA | 1.02353 |
| 7 | Bilateral or >2 on biopsy | 1.61176 |
| 8 | Bilateral cancer on biopsy | 0.08235 |

TABLE 4-continued

| | | |
|---|---|---|
| 9 | Cancer >2 cores on biopsy | 0.61176 |
| 10 | Perineural infiltration | 0.58824 |
| 11 | Log Gleason Weighted PSA | 0.18824 |
| 12 | Biopsy Gleason | 1.51765 | b. Seminal Vesicle Positivity Results

Figure 3A:
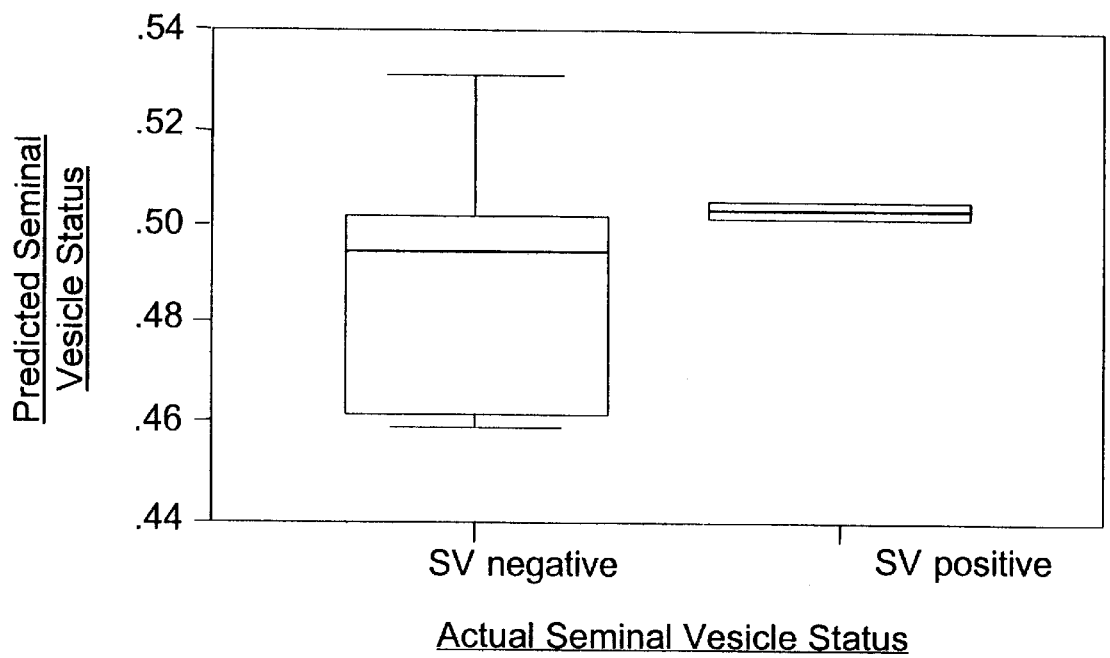
FIGS. 3a–3b. Box plot and ROC analysis of network output (continuous) for seminal vesicle positivity. The accuracy was always better by Bayesian theorem analysis.
Figure 3B:
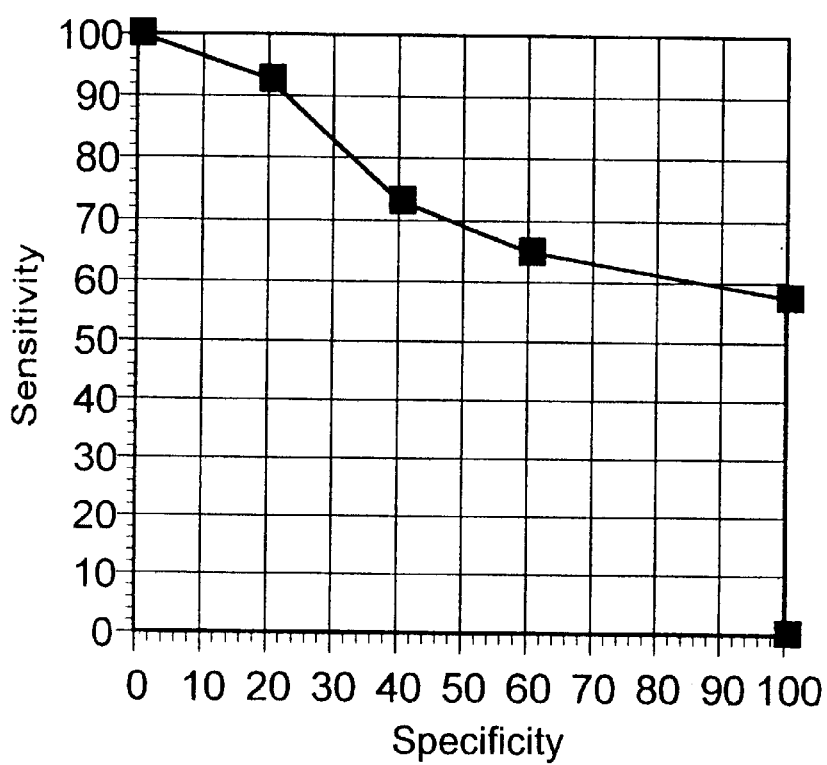

Results with respect to seminal vesicle positivity can be seen in Table 5 and FIGS. 3a–3b. (Input variables are shown in Table Prevalence of S.V. positivity in the sample was 3.9%. Neural net sensitivity and specificity for this feature were 100.0% and 72.1%, respectively, with corresponding 95% lower confidence bounds of 56.0% and 63.3%. Sample-specific positive and negative predictive values were 12.8% and 100.0%, respectively, with corresponding 95% lower confidence bounds of 4.3% and 97.0%, respectively.

TABLE 5

Neural net predicted probabilities (Bayesian theorem) of seminal vesicle vs. ROC prediction of network output ("O-1" indicates neural net binary prediction) in production set

| Cutoffs | Positive patients | | Negative patients | | | Accuracy percentages | | | |
|---|---|---|---|---|---|---|---|---|---|
| Probability Level | Neural Net Right | Neural Net Wrong | Neural Net Right | Neural Net Wrong | Overall Accuracy | Sensitivity | Specificity | PPV | NPV |
| 0.000 | 5 | 0 | 0 | 122 | 3.9 | 100.0 | 0.0 | 3.9 | — |
| 0.497 | 5 | 0 | 70 | 52 | 59.1 | 100.0 | 57.4 | 8.8 | 100.0 |
| 0.499 | 3 | 2 | 79 | 43 | 64.6 | 60.0 | 64.8 | 6.5 | 97 |
| 0.500 | 2 | 3 | 89 | 33 | 71.7 | 40.0 | 73.0 | 5.7 | 96 |
| 0.510 | 1 | 4 | 113 | 9 | 89.8 | 20.0 | 92.6 | 10.0 | 96 |
| 1.000 | 0 | 5 | 122 | 0 | 96.1 | 0.0 | 100.0 | — | 96 |
| ROC: 0-1 | | Lower 95% Bound: | | | 64.6 | 56.0 | 63.3 | 4.3 | 97 |
| PNN 0/1 | 5 | 0 | 88 | 34 | 73.2 | 100.0 | 71.1 | 12.0 | 108 |

Sample specific prevalence of seminal vesicle positivity - 5/127 = 3.9%
ROC: Receiver operator curves
PNN: Probabilistic Neural Network
Area under the curve (AUC): .804

Overall, the network labeled 69% (88/127) of patients as negative for seminal vesicle involvements, and its predictions were never wrong in this small set of patients. There were 31% (39/127) patients who were labeled positive, and 87% (PPV=13%) of these patients actually did not have seminal vesicle disease. Therefore, the utility of the network in this 31% (labeled positive) of patients was not useful. However, the high negative predictive value allows it to be an excellent initial staging tool which can preclude any additional testing in approximately 69% of patients who can directly proceed for definitive radical therapy. The margin of error in this approach is 0% and will save up to 69% of staging cost towards pelvic CT, E-MRI, and S.V. biopsy.

Parameters of interest in this analysis are shown in Table 6. With respect to seminal vesicle involvement, the teaching data preferably comprises at least one of three inputs, namely, log biopsy weighted PSA, log Gleason weighted PSA and biopsy Gleason. Smoothing factors are again appropriately applied.

TABLE 6

| Network type | PNN, genetic adaptive |
|---|---|
| Problem name | C:\STAGENET\SVNET\SVNET |
| Number of inputs | 3 |
| Number of outputs | 2 |
| Number of training patterns | 166 |
| Number of test patterns | 135 |

| smoothing test individuals | |
|---|---|
| current best smoothing factor | 0.3171765 |
| smoothing test generations | 70 |
| last number incorrect | 12.07946 |
| minimum number incorrect | 12.0788 |
| generations since min. incorrect | 20 |

TABLE 6-continued

| Input# | Input name | Individual smoothing factor |
|---|---|---|
| 1 | Log Biopsy Weighted PSA | 0.56471 |
| 2 | Log Gleason Weighted PSA | 2.90588 |
| 3 | Biopsy Gleason | 1.34118 | c. Lymph Node Positivity Results

Figure 4A:
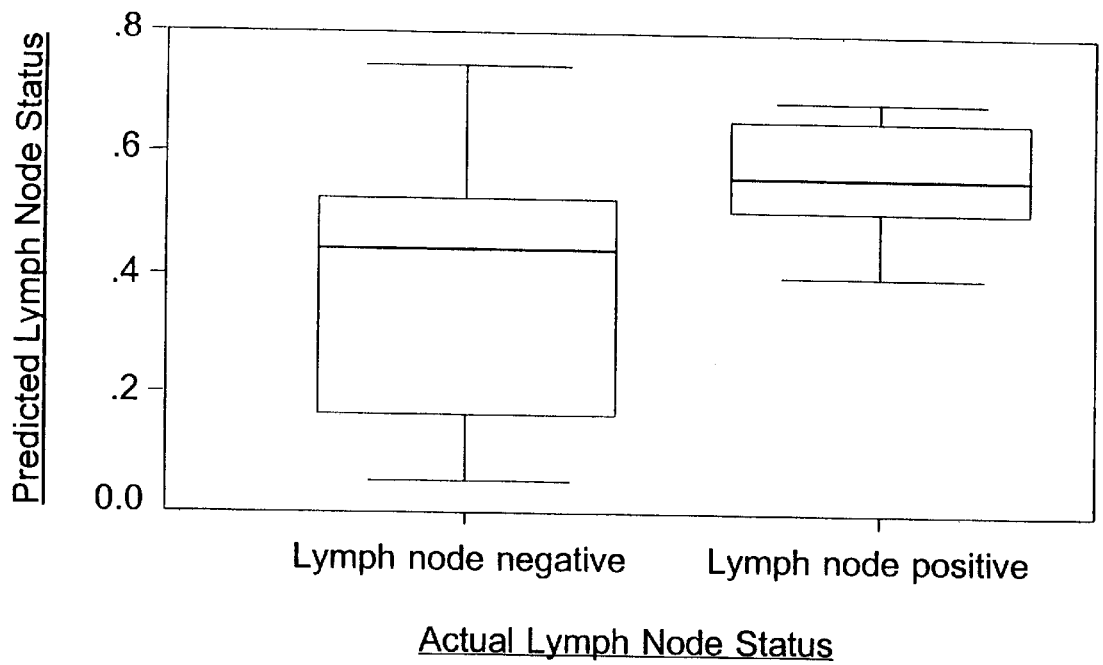
FIGS. 4a–4b. Box plot and ROC analysis of network output (continuous) for lymph node positivity. The accuracy was always better by Bayesian theorem analysis.
Figure 4B:
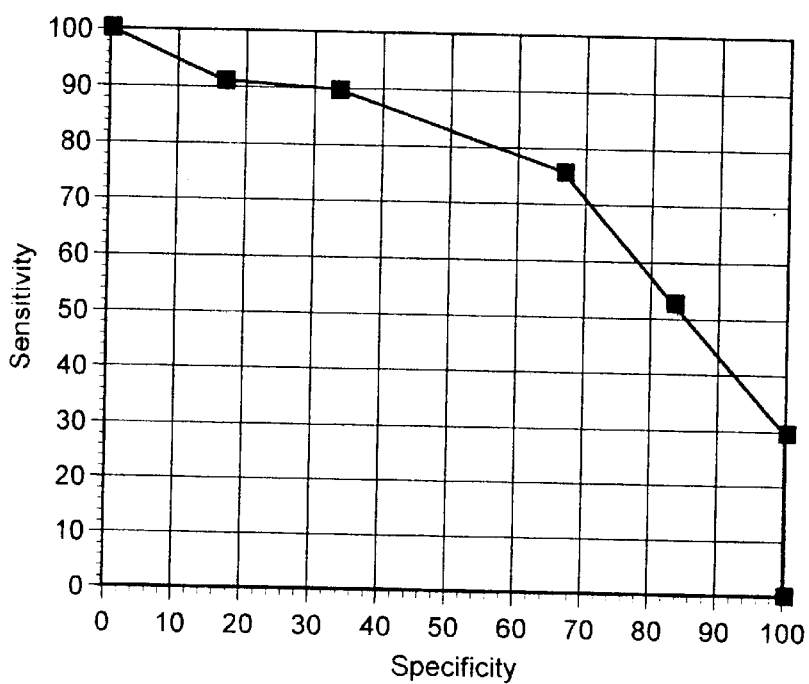

The results with regard to lymph node positivity can be seen in Table 7 and FIGS. 4a–4b. Prevalence of this feature in the sample was 7.1%. Neural net sensitivity and specificity for this feature were 83.3% and 71.8%, respectively, with corresponding 95% lower confidence bounds of 35.9% and 60.5%. Sample-specific positive and negative predictive values were 18.5% and 98.2%, respectively. Thus, 81.5% of patients designated as positive by the neural network in actuality did not require further testing, while 1.8% of patients designated as negative by the neural network actually required further testing.

TABLE 7

Neural net predicted probabilities (Bayesian theorem) of lymph node vs. ROC prediction of network output ("O-1" indicates neural net binary prediction) in production set

| Cutoffs Probability Level | Positive patients | | Negative patients | | Overall Accuracy | Accuracy percentages | | | |
|---|---|---|---|---|---|---|---|---|---|
| | Neural Net Right | Neural Net Wrong | Neural Net Right | Neural Net Wrong | | Sensitivity | Specificity | PPV | NPV |
| 0.000 | 6 | 0 | 0 | 78 | 7.1 | 100.0 | 0.0 | 7.1 | — |
| 0.285 | 6 | 0 | 23 | 55 | 34.5 | 100.0 | 29.5 | 9.8 | 100 |
| 0.467 | 5 | 1 | 41 | 37 | 54.8 | 83.3 | 52.6 | 11.9 | 97 |
| 0.527 | 4 | 2 | 59 | 19 | 75.0 | 66.7 | 75.6 | 17.4 | 96 |
| 0.596 | 2 | 4 | 70 | 8 | 85.7 | 33.3 | 89.7 | 20.0 | 94 |
| 0.627 | 1 | 5 | 71 | 7 | 85.7 | 16.7 | 91.0 | 12.5 | 93 |
| 1.000 | 0 | 6 | 78 | 0 | 92.9 | 0.0 | 100.0 | — | 92 |
| ROC: 0-1 | | Lower 95% Bound: | | | 61.8 | 35.9 | 60.5 | 6.3 | 90 |
| PNN 0/1 | 5 | 1 | 56 | 22 | 72.6 | 83.3 | 71.8 | 18.5 | 98 |

Sample specific prevalence of positive lymph nodes - 6/84 = 7.1%
ROC: Receiver operator curves
PNN: Probabilistic Neural Network
Area under the curve (AUC): .768

Overall, the network labeled 68% (57/84) of all patients as negative for lymph nodal disease, and predictions were wrong in only 2% of patients in this study. Thirty-two percent (27/84) of the patients were labeled positive by the network, but only 18% of these actually had lymph nodal disease. Therefore, the utility of the network in this 32% (labeled positive) of patients was not useful. However, high negative predictive value allows it to be an excellent initial staging tool which can preclude any additional testing in approximately 68% of patients who can directly proceed for definitive radical therapy. The margin of error in this approach is 2% and will save up to 68% of staging cost toward pelvic CT, E-MRI, and LND.

Parameters of interest in this analysis are shown in Table 8. With respect to lymph nodal involvement, the teaching data preferably comprises at least one of six inputs, namely, race code, PSA/age ratio, TRUS code, log biopsy weighted PSA, log Gleason weighted PSA, and biopsy Gleason.

TABLE 8

| Network type | PNN, genetic adaptive |
|---|---|
| Problem name | C:\STAGENET\LNNET\LNNET |
| Number of inputs | 6 |
| Number of outputs | 2 |
| Number of training patterns | 166 |
| Number of test patterns | 135 |

| smoothing test individuals | |
|---|---|
| current best smoothing factor | 0.0682353 |
| smoothing test generations | 88 |
| last number incorrect | 6.036187 |
| minimum number incorrect | 6.036146 |
| generations since min. incorrect | 21 |

| Input# | Input name | Individual smoothing factor |
|---|---|---|
| 1 | Race Code | 1.72941 |
| 2 | PSA/Age Ratio | 1.16471 |
| 3 | TRUS Code | 2.44706 |
| 4 | Log Biopsy Weighted PSA | 1.22353 |
| 5 | Log Gleason Weighted PSA | 2.44706 |
| 6 | Biopsy Gleason | 2.02353 |

Staging Algorithm

Figure 5:
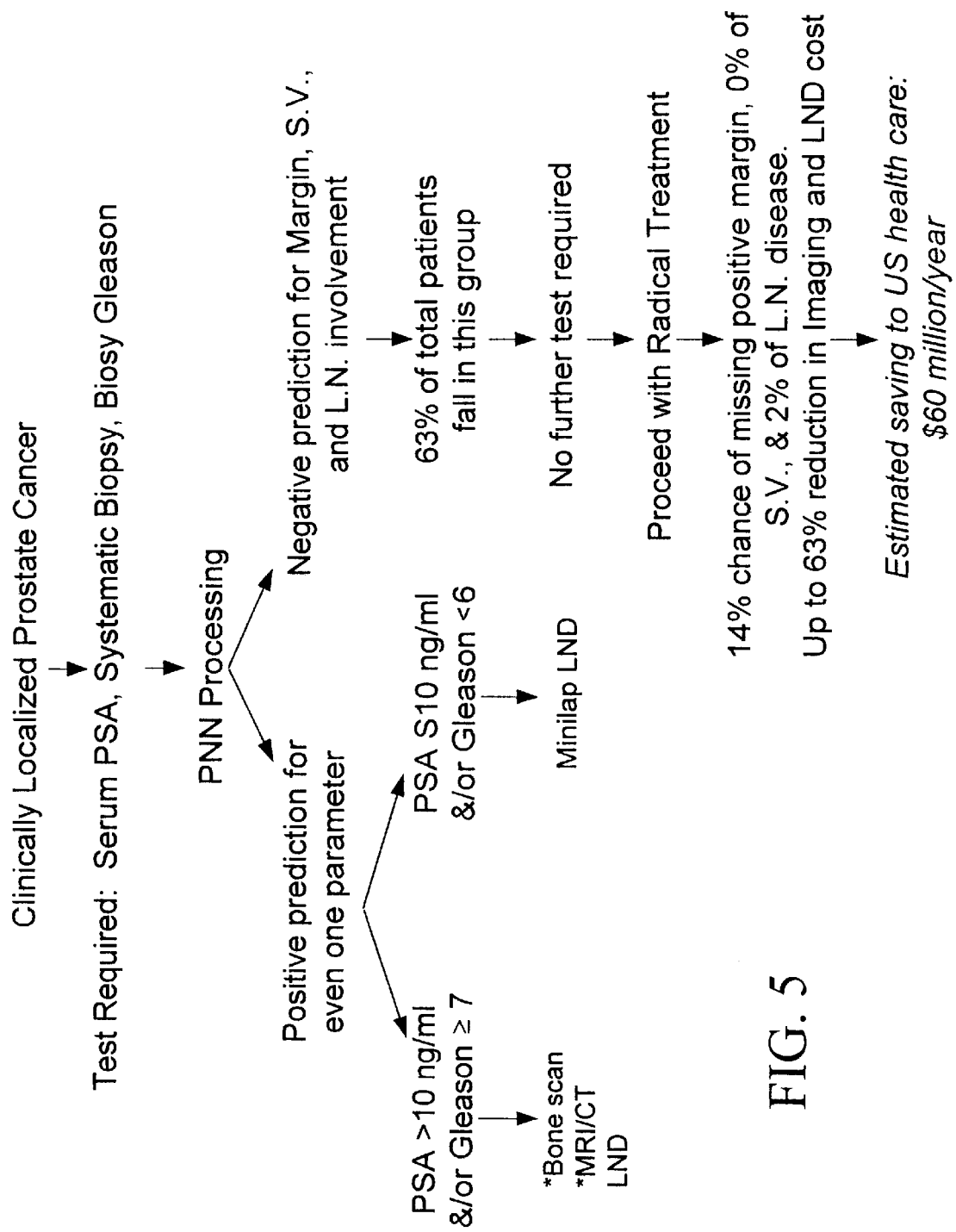
FIG. 5. Cost-effective staging algorithm: Showing detailed staging protocol. Note that >60% of patients did not require additional testing.

As can be seen in FIG. 5, overall, the network labeled 63% of patients negative for margin positivity, seminal vesicle involvement, and lymph nodal disease. The margin of error in these patients was <15% for margin positive disease, 2% for lymph nodal disease, and 0% for seminal vesicle involvement. Therefore, if we avoid any additional staging tests in this 63% of patients who are labeled as negative by the network, we will actually save up to 63% in staging costs by not performing pelvic CT, E-MRI, lymph nodal dissection, and capsular and S.V. biopsy. However, the patients who are labeled positive (37%) will require additional testing.

Specific Example 2—Diagnosing a Patient Using Trained Neural Network

Once trained, the neural network can be used to diagnose an individual patient. First, clinical testing was conducted to obtain preoperative serum PSA, biopsy Gleason score, and systemic biopsy-based information for the patient. Specifically, the patient was 56 years old, had a PSA of 7.8, a Gleason score of 8, bilateral cancer on biopsy and perineural infiltration. This data formed the primary inputs to the neural network. Secondary patient data inputs were then automatically calculated by the computer. Any necessary smoothing factors were automatically applied by the computer. The network then provided an output variable for a pathological feature in question, namely margin positivity of 86%, seminal vesicle involvement of 28%, and lymph nodal involvement of 38%. For each of the pathological features in question, the inputs to the neural network varied as during the training set forth in Example 1 and in the Tables associated therewith.

Specific Example 3—Training and Using Network to Predict Biochemical Failure Following Radical Prostatectomy Biochemical failure following radical prostatectomy occurs in as many as 58% of patients with positive margins, 57% with seminal vesicle disease and 100% with lymph node disease. For proper monitoring and postoperative treatment, it is desirable to predict early on as to which patients are likely to recur. A neural network model was designed for early prediction of biochemical recurrence.

Training: 146 patients with localized prostate cancer who underwent systematic biopsy based staging, serum PSA estimation prior to radical prostatectomy and had a mean post operative follow up of 59.8 months (12–118 months) during which they had serial PSA estimation, form the subjects of this study. Patients underwent total bone scintigraphy and TRUS guided biopsy of the prostatic fossa if they developed a rising PSA. Failure was defined as a change from an undetectable to a detectable level of PSA or a serial increase of PSA from any detectable level 2 months after surgery. Using preoperative PSA, Gleason score, systematic biopsy data and pathological staging findings, a probabilistic neural network was trained on 90 patients and tested on 56 patients to predict 5 year biochemical failure.

Results: The overall accuracy of this Neural Network was 86% and area under the curve on receiver operator curve (ROC) was 0.9395.

|  | Sensitivity | Specificity | PPV | NPV |
| --- | --- | --- | --- | --- |
| PSA failure | 79% | 91% | 86% | 85% |

Conclusions: Neural Network technology can be used to model a predicting tool for detection of biochemical failure following radical prostatectomy. Initial results suggest that this network is highly accurate and superior to standard statistical methodologies.

Based on the discussion herein, we have formulated a staging protocol in which every patient suspected of having prostate cancer undergoes TRUS-guided systemic biopsy and additional biopsies of suspicious areas, S.V., and capsule if indicated. Following this, all patients initially undergo staging using PNN's staging using serum PSA, biopsy Gleason, and systemic biopsy based staging as primary input variables. Other input variables can be automatically calculated by the computer. It is expected that, based on the proposed protocol, 63% of all patients will not need any further investigation.

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. A method for evaluating the stage of prostate cancer in a patient wherein said method comprises use of a neural network, wherein said neural network provides prostate cancer stare information for said patient based upon input data, wherein said input data includes the patient's preoperative serum PSA, biopsy Gleason score, and systemic biopsy-based information, wherein said prostate cancer stage information is provided as an output variable comprising margin positivity, seminal vesicle involvement, and lymph nodal involvement.

2. The method of claim 1, wherein said neural network is trained by clinical testing of a test population of patients with prostate cancer to obtain teaching data, said teaching data comprising preoperative serum PSA, biopsy Gleason score, and systemic biopsy-based information; calculating secondary data based on said teaching data; and inputting said teaching data and said secondary data into said neural network, whereby said neural network is trained to provide an output variable corresponding to the stage of prostate cancer.

3. The method of claim 1, further comprising calculating secondary patient input data for said margin positivity output variable, wherein said secondary patient input data is from one or more of race code, DRE code, a PSA to age ratio, log of PSA, TRUS code, a log of biopsy weighted PSA, a bilateral or greater than 2 on biopsy, a bilateral cancer on biopsy, a cancer greater than 2 cores on biopsy, perineural infiltration, a log Gleason weighted PSA, and a biopsy Gleason.

4. The method of claim 1, further comprising calculating secondary patient input data for said seminal vesicle involvement output variable, wherein said secondary patient input data is from one or more of log biopsy weighted PSA, log Gleason weighted PSA and biopsy Gleason.

5. The method of claim 1, further comprising calculating secondary patient input data for said lymph nodal involvement output variable, wherein said secondary patient input data is from one or more of race code, PSA/age ratio, TRUS code, log biopsy weighted PSA, log Gleason weighted PSA, and biopsy Gleason.

6. A method for developing a treatment plan for a patient with prostate cancer wherein said method comprises providing input data to a trained neural network wherein said input data comprises the patient's preoperative serum PSA, biopsy Gleason score, and systemic biopsy-based information; wherein said method further comprises utilizing output information provided by said neural network to formulate said treatment plan.

7. A system for diagnosing prostate cancer in a patient comprising a neural network which first receives as input primary teaching data obtained from clinical testing of a test population of patients with prostate cancer and secondary teaching data based on said primary teaching data whereby said neural network learns said teaching data and is trained to provide an output variable for a pathological feature in question, wherein said output variable comprises margin positivity, seminal vesicle involvement, and lymph nodal involvement, such that when said neural network receives primary patient input data obtained from clinical testing of a patient to be diagnosed and calculates secondary patient input data based on said primary patient input data, said neural network provides said output variable for diagnosis of said pathological feature in question for said patient.

8. A system for diagnosing prostate cancer in a patient comprising a trained neural network, wherein said neural network was trained by inputting teaching data obtained from clinical testing of a test population of patients with prostate cancer to provide an output variable for a pathological feature in question, such that when said neural network receives primary patient input data obtained from clinical testing of a patient to be diagnosed and calculates secondary patient input data based on said primary patient input data, said neural network provides said output variable for diagnosis of said pathological feature in question for said patient, wherein said output variable comprises margin positivity, seminal vesicle involvement, and lymph nodal involvement.

9. A method for diagnosing prostate cancer in a patient comprising the steps of:

a) selecting a plurality of clinical parameters for a pathological feature in question;

b) converting said clinical parameters into numerical expressions;

c) inputting said numerical expressions into a neural network to train said neural network to provide an output variable for a pathological feature in question;

d) obtaining from a patient said plurality of clinical parameters;

e) converting said clinical parameters into numerical expressions; and f) inputting said numerical expressions into said neural network to obtain said output variable for diagnosing prostate cancer in said patient;

wherein said output variable comprises margin positivity, seminal vesicle involvement, and lymph nodal involvement.

10. The method of claim 9, wherein said clinical parameters comprise preoperative serum PSA, biopsy Gleason score, and systemic biopsy-based information.

11. The method of claim 9 wherein for said margin positivity output variable, said numeral expressions include secondary input data from one or more of race code, DRE code, a PSA to age ratio, log of PSA, TRUS code, a log of biopsy weighted PSA, a bilateral or greater than 2 on biopsy, a bilateral cancer on biopsy, a cancer greater than 2 cores on biopsy, perineural infiltration, a log Gleason weighted PSA, and a biopsy Gleason; and further wherein for said seminal vesicle involvement output variable, said numeral expressions include secondary input data from one or more of log biopsy weighted PSA, log Gleason weighted PSA and biopsy Gleason; and further wherein for said lymph nodal involvement output variable, said numeral expressions include secondary input data from one or more of race code, PSA/age ratio, TRUS code, log biopsy weighted PSA, log Gleason weighted PSA, and biopsy Gleason.

12. A method for diagnosing prostate cancer in a patient comprising the steps of:
   a) clinical testing of a test population of patients with prostate cancer to obtain primary teaching data;
   b) calculating secondary teaching data based on said primary teaching data;
   c) inputting said primary and secondary teaching data into a neural network for use in diagnosing patients and causing said neural network to learn said teaching data, whereby said neural network is trained to provide an output variable for a pathological feature in question, wherein said output variable comprises margin positivity, seminal vesicle involvement, and lymph nodal involvement;
   d) clinical testing of patient to be diagnosed to obtain primary patient input data;
   e) calculating secondary patient input data based on said primary patient input data;
   f) inputting said primary and secondary patient input data into said neural network; and
   g) obtaining a diagnosis for said pathological feature in question for said patient from said output variable for said neural network.

13. A method for diagnosing prostate cancer in a patient utilizing a trained neural network wherein said neural network was trained by clinical testing of a test population of patients with prostate cancer to obtain primary teaching data; calculating secondary teaching data based on said primary teaching data; and inputting said primary and secondary teaching data into a neural network for use in diagnosing patients whereby said neural network is trained to provide an output variable for a pathological feature in question, comprising the steps of:
   a) clinical testing of patient to be diagnosed to obtain primary patient input data;
   b) calculating secondary patient input data based on said primary patient input data;
   c) inputting said primary and secondary patient input data into said neural network; and
   d) obtaining a diagnosis for said pathological feature in question for said patient from said output variable of said neural network;
wherein said output variable comprises margin positivity, seminal vesicle involvement, and lymph nodal involvement.

14. The method of claim 13, wherein said primary patient input data comprises preoperative serum PSA, biopsy Gleason score, and systemic biopsy-based information.

15. The method of claim 13, wherein for said margin positivity output variable, said secondary patient input data is from one or more of race code, DRE code, a PSA to age ratio, log of PSA, TRUS code, a log of biopsy weighted PSA, a bilateral or greater than 2 on biopsy, a bilateral cancer on biopsy, a cancer greater than 2 cores on biopsy, perineural infiltration, a log Gleason weighted PSA, and a biopsy Gleason.

16. The method of claim 13, wherein for said seminal vesicle involvement output variable, said secondary patient input data is from one or more of log biopsy weighted PSA, log Gleason weighted PSA and biopsy Gleason.

17. The method of claim 13, wherein for said lymph nodal involvement output variable, said secondary patient input data is from one or more of race code, PSA/age ratio, TRUS code, log biopsy weighted PSA, log Gleason weighted PSA, and biopsy Gleason.

18. A method for diagnosing prostate cancer in a patient utilizing a trained neural network wherein said neural network was trained by clinical testing of a test population of patients with prostate cancer to obtain primary teaching data; calculating secondary teaching data based on said primary teaching data; and inputting said primary and secondary teaching data into a neural network for use in diagnosing patients whereby said neural network is trained to provide an output variable for a pathological feature in question, comprising the steps of:
   a) clinical testing of patient to be diagnosed to obtain primary patient input data;
   b) calculating secondary patient input data based on said primary patient input data;
   c) inputting said primary and secondary patient input data into said neural network; and
   d) obtaining a diagnosis for said pathological feature in question for said patient from said output variable of said neural network;
further comprising applying smoothing factors to said input data.

19. A method for diagnosing prostate cancer in a patient utilizing a trained neural network wherein said neural network was trained by clinical testing of a test population of patients with prostate cancer to obtain primary teaching data; calculating secondary teaching data based on said primary teaching data; and inputting said primary and secondary teaching data into a neural network for use in diagnosing patients whereby said neural network is trained to provide an output variable for a pathological feature in question, comprising the steps of:
   a) clinical testing of patient to be diagnosed to obtain primary patient input data;
   b) calculating secondary patient input data based on said primary patient input data;
   c) inputting said primary and secondary patient input data into said neural network; and
   d) obtaining a diagnosis for said pathological feature in question for said patient from said output variable of said neural network;
wherein said output variable comprises binary probability predictions and continuous probability predictions.

20. A method for training a neural network for diagnosing prostate cancer in a patient comprising the steps of:
   a) clinical testing of a test population of patients with prostate cancer to obtain primary teaching data, said primary teaching data comprising preoperative serum PSA, biopsy Gleason score, and systemic biopsy-based information;

b) calculating secondary teaching data based on said primary teaching data; and c) inputting said primary and secondary teaching data into a neural network for use in diagnosing patients and causing said neural network to learn said teaching data, whereby said neural network is trained to provide an output variable for a pathological feature in questions; wherein said secondary teaching data comprises ratios and logarithms of said primary teaching data and said primary patient input data respectively.

21. The method of claim 20, wherein said secondary teaching data is from one or more of a log 10 of serum PSA, a weighting of said PSA, a ratio of said PSA and said biopsy-based information, a ratio of said PSA with said Gleason score, and an aggressive or non-aggressive factor based on said PSA, said Gleason score and said biopsy-based information.

22. The method of claim 20, wherein said neural network is a probabilistic three-layer neural network possessing an input layer, a hidden layer, and an output layer, based on Bayesian theory which separates data into a specified number of output categories.

23. The method of claim 20, wherein said neural network is trained based on genetic adaptive algorithms using calibration to testing smoothing factors as individual multipliers for each of said input data.

24. The method of claim 20, further comprising subjecting said continuous probability predictions to nonparametric receiver-operator characteristic curve (ROC) analysis.

25. The method of claim 20, further comprising the step of excluding test patients unable to undergo TRUS-guided biopsy, had preoperative hormonal radiation, or cryotherapy, or did not undergo pelvic lymphadenectomy.

26. A method for predicting biochemical failure following radical prostatectomy in a patient wherein said method comprises use of a neural network wherein said neural network provides a predicting tool for detection of biochemical failure of said patient based upon input data wherein said input data includes the patient's preoperative serum PSA, biopsy Gleason score, and systemic biopsy-based information.

* * * * *

UNITED STATES PATENT AND TRADEMARK OFFICE
CERTIFICATE OF CORRECTION

PATENT NO. : 6,004,267
DATED : December 21, 1999
INVENTOR(S) : Ashutosh Tewari, Perinchery Narayan It is certified that error appears in the above-identified patent and that said Letters Patent is hereby corrected as shown below:

Column 2, line 13: "205-21;" should read --205-212;--.

Column 6, line 6: "Diagrarmmatic" should read --Diagrammatic--.

Column 11, line 29: "sigtnoidal" should read --sigmoidal--.

Column 21, line 42: "stare" should read --stage--.

Signed and Sealed this

Twelfth Day of September, 2000

Attest:

Q. TODD DICKINSON

*Attesting Officer*          *Director of Patents and Trademarks*